(12) United States Patent
Margoosian et al.

(10) Patent No.: US 9,724,437 B2
(45) Date of Patent: Aug. 8, 2017

(54) HEAT STERILIZATION TECHNIQUES FOR CHLORHEXIDINE BASED ANTISEPTIC FORMULATIONS

(71) Applicant: LERNAPHARM (LORIS) INC., Ville St-Laurent (CA)

(72) Inventors: Razmik Margoosian, Montreal (CA); Viken Afarian, Laval (CA)

(73) Assignee: LERNAPHARM (LORIS) INC., Ville St-Laurent, Quebec (CA)

( * ) Notice: Subject to any disclaimer, the term of this patent is extended or adjusted under 35 U.S.C. 154(b) by 441 days.

(21) Appl. No.: 13/962,317

(22) Filed: Aug. 8, 2013

(65) Prior Publication Data
US 2014/0322072 A1     Oct. 30, 2014

(51) Int. Cl.
*A61L 2/04* (2006.01)
*A61L 2/00* (2006.01)
*A61L 2/28* (2006.01)

(52) U.S. Cl.
CPC .............. *A61L 2/04* (2013.01); *A61L 2/0023* (2013.01); *A61L 2/28* (2013.01)

(58) Field of Classification Search
CPC ............. A61L 2/04; A61L 2/0023; A61L 2/28
See application file for complete search history.

(56) References Cited

U.S. PATENT DOCUMENTS

| | | | | |
|---|---|---|---|---|
| 2,318,380 A | * | 5/1943 | Davis et al. .................... 53/430 |
| 3,324,723 A | * | 6/1967 | Ritchie ..................... A61L 2/28 |
| | | | | 116/217 |
| 3,618,283 A | * | 11/1971 | Moore et al. ................... 53/431 |
| 3,946,611 A | * | 3/1976 | Larsson .................... G01K 3/04 |
| | | | | 116/216 |
| 3,999,946 A | * | 12/1976 | Patel ..................... G01N 31/229 |
| | | | | 252/962 |
| 4,042,336 A | * | 8/1977 | Larsson .................... G01K 3/04 |
| | | | | 116/216 |
| 4,050,894 A | * | 9/1977 | Genis ........................... 206/363 |
| 4,138,216 A | * | 2/1979 | Larsson ............... G01N 31/226 |
| | | | | 252/962 |
| 4,169,123 A | | 9/1979 | Moore et al. |
| 4,169,124 A | * | 9/1979 | Forstrom ............... A01N 59/00 |
| | | | | 422/28 |
| 4,206,844 A | * | 6/1980 | Thukamoto .......... A61B 19/026 |
| | | | | 206/439 |
| 4,382,063 A | * | 5/1983 | Romito ................ G01N 31/226 |
| | | | | 116/207 |

(Continued)

FOREIGN PATENT DOCUMENTS

GB     WO 2013179055 A1 *  12/2013  .......... A61M 35/003

OTHER PUBLICATIONS

U.S. Appl. No. 61/836,052, filed Jun. 17, 2013.*

(Continued)

*Primary Examiner* — Regina M Yoo
(74) *Attorney, Agent, or Firm* — SmithAmundsen LLC; Stephen L. Farris; Douglas G. Gallagher

(57) ABSTRACT

Techniques for sterilizing chlorhexidine based antiseptic formulations include exposing a sealed container containing the formulation to heat at a temperature and heating time sufficient to sterilize the chlorhexidine based antiseptic formulation and the hermetically sealed interior of the container, which may be an applicator, a bottle, a swab stick, or a pad-containing pouch.

27 Claims, 2 Drawing Sheets

(56) References Cited

U.S. PATENT DOCUMENTS

| | | | |
|---|---|---|---|
| 5,357,636 A * | 10/1994 | Dresdner et al. | 2/161.7 |
| 5,476,792 A * | 12/1995 | Ezrielev | G01K 11/06 116/219 |
| 5,573,800 A * | 11/1996 | Wilhoit | 426/326 |
| 5,573,801 A * | 11/1996 | Wilhoit | 426/326 |
| 5,690,958 A * | 11/1997 | McGrath | 424/451 |
| 5,752,363 A * | 5/1998 | Edwards et al. | 53/410 |
| 5,772,346 A * | 6/1998 | Edwards | 401/132 |
| 6,139,794 A * | 10/2000 | Asgharian et al. | 422/1 |
| 6,485,978 B1 * | 11/2002 | Kirckof | A61L 2/28 422/403 |
| 6,595,940 B1 * | 7/2003 | D'Alessio et al. | 604/3 |
| 7,199,090 B2 * | 4/2007 | Koivisto | A01N 31/02 510/130 |
| 7,637,679 B2 * | 12/2009 | May et al. | 401/133 |
| 7,704,935 B1 * | 4/2010 | Davis | A01N 31/02 510/130 |
| 8,118,508 B2 * | 2/2012 | Goodman et al. | 401/133 |
| 8,652,510 B2 * | 2/2014 | Zhang | A61L 24/00 424/443 |
| 2002/0037546 A1 * | 3/2002 | Hendricks | A61L 2/28 435/31 |
| 2004/0120849 A1 * | 6/2004 | Stewart et al. | 422/22 |
| 2005/0262811 A1 * | 12/2005 | Mohiuddin | 53/425 |
| 2005/0267423 A1 * | 12/2005 | Johnson et al. | 604/295 |
| 2007/0276312 A1 * | 11/2007 | Davis et al. | 604/3 |
| 2012/0003029 A1 * | 1/2012 | Guzman et al. | 401/133 |
| 2012/0184929 A1 * | 7/2012 | Davis et al. | 604/310 |
| 2013/0156640 A1 | 6/2013 | Kohler et al. | |
| 2013/0193008 A1 * | 8/2013 | Reyhan et al. | 206/205 |
| 2013/0202482 A1 * | 8/2013 | Froimson | A61M 35/006 422/28 |
| 2013/0252340 A1 * | 9/2013 | Haertling | A61L 2/087 436/1 |
| 2013/0310755 A1 * | 11/2013 | Zhang | A61L 24/00 604/180 |
| 2014/0057864 A1 * | 2/2014 | Kim | 514/46 |
| 2014/0366485 A1 * | 12/2014 | Chiang et al. | 53/416 |
| 2014/0371694 A1 * | 12/2014 | Chiang et al. | 604/310 |

OTHER PUBLICATIONS

Gershenfeld, L., Providone-Iodine as a Sporicide, American Journal of Pharmacy, Mar. 1962, p. 78-81, vol. 134, Philadelphia, USA.

Graham W. Denton; Chlorhexidine; Disinfection, Sterilization, and Preservation; 2001; 321-324,327 ; Fifth Edition; Lippincott Williams & Wilkins; Philadelphia, PA.

* cited by examiner

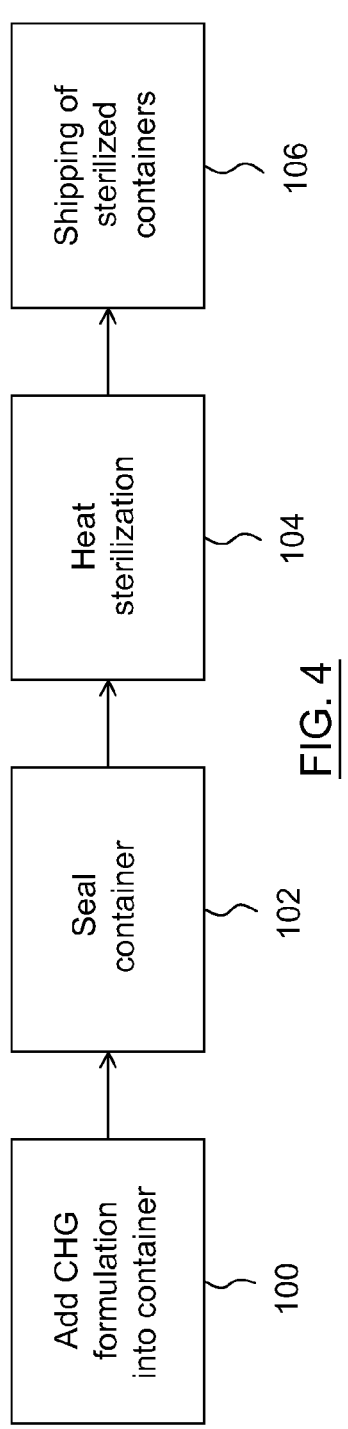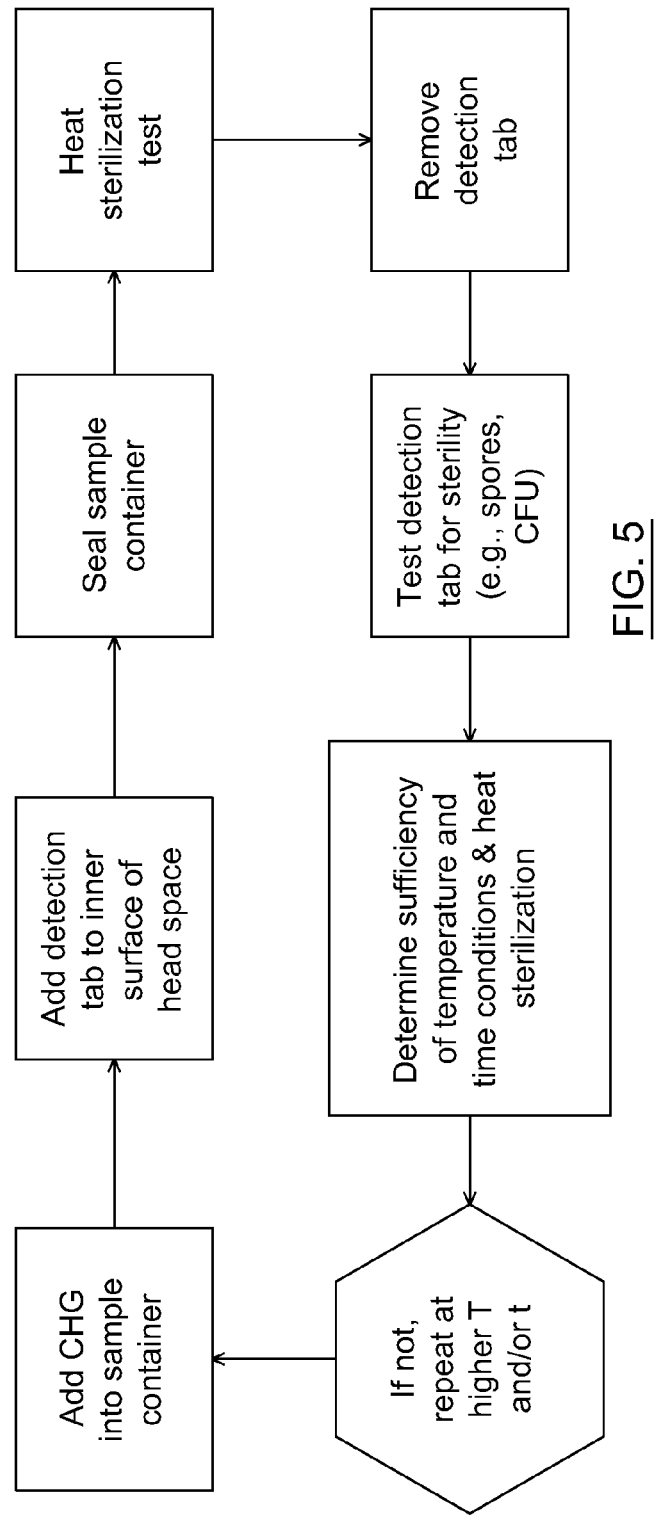

HEAT STERILIZATION TECHNIQUES FOR CHLORHEXIDINE BASED ANTISEPTIC FORMULATIONS

FIELD OF THE INVENTION

The present invention generally relates to the field of antiseptic formulations, and more particularly, to techniques for sterilizing chlorhexidine based antiseptic formulations.

BACKGROUND OF THE INVENTION

Antiseptic formulations are often used in the context of surgery for topical cleaning or other medical uses. Antiseptic formulations may be provided in containers, applicators, swabs, or via other delivery means.

In the manufacturing and use of antiseptic formulations and associated vessels, there are various challenges related to providing and maintaining sterility. Some methods of making sterile products are aseptic processing and terminal sterilization. Each of these general methods has various drawbacks and challenges when applied to certain antiseptic formulations and associated vessels.

SUMMARY OF THE INVENTION

Various techniques are described for sterilizing chlorhexidine based antiseptic formulations.

In some implementations, there is provided a process for preparing and sterilizing a chlorhexidine based antiseptic formulation and a container for medical use, the process comprising: adding the chlorhexidine based antiseptic formulation into the container; hermetically sealing the container to form a sealed container having a hermetically sealed interior; and exposing the sealed container to heat at a temperature and heating time sufficient to sterilize the chlorhexidine based antiseptic formulation and the hermetically sealed interior of the container.

In some implementations, the sealed container comprises a first region holding the chlorhexidine based antiseptic formulation and a second region comprising air and vapour from the chlorhexidine based antiseptic formulation.

In some implementations, the chlorhexidine based antiseptic formulation comprises a solvent.

In some implementations, the chlorhexidine based antiseptic formulation comprises purified water.

In some implementations, the chlorhexidine based antiseptic formulation comprises an additional active component. In some implementations, the additional active component is miscible in water. In some implementations, the additional active component comprises an alcohol. In some implementations, the alcohol is a secondary alcohol having a single hydroxyl group. In some implementations, the additional active component is isopropyl alcohol. In some implementations, the isopropyl alcohol is present in a concentration between about 55% v/v and about 80% v/v of the chlorhexidine based antiseptic formulation.

In some implementations, the chlorhexidine is chlorhexidine gluconate. In some implementations, the chlorhexidine based antiseptic formulation comprises about 0.5% w/v to about 5% w/v of the chlorhexidine gluconate. In some implementations, the chlorhexidine based antiseptic formulation comprises about 1.5% w/v to about 2.5% w/v of the chlorhexidine gluconate.

In some implementations, the temperature is at least about 62° C. and the heating time period is at least about 12 hours.

In some implementations, the container is a liquid applicator. In some implementations, the liquid applicator comprises: the container as a container body component; and a head component comprising an absorbent material, the head component being cooperable with the container body component in order to break a portion of the container body component and allow the formulation to flow from the container body component through the head component and into the absorbent material for application.

In some implementations, the temperature is at least about 62° C. and the heating time period is at least about 12 hours. In some implementations, the temperature is between about 55° C. and about 70° C. and the heating time period is at least 9 hours. In some implementations, the temperature is between about 55° C. and about 70° C. and the heating time period is at least 16 hours. In some implementations, the temperature is between about 55° C. and about 70° C. and the heating time period is at least 24 hours. In some implementations, the temperature is between about 55° C. and about 70° C. and the heating time period is between 9 hours and 36 hours. In some implementations, the temperature is between about 60° C. and about 67° C. and the heating time period is at least 12 hours.

In some implementations, the process also includes determining sterilization conditions comprising: adding the chlorhexidine based antiseptic formulation into a sample container having inner surfaces; applying a detection tab to an inner surface of the container; hermetically sealing the sample container; exposing the sealed sample container to a set of temperature and heating time conditions; removing the detection tab after heat treatment; testing the detection tab for sterility; and determining from results of the testing step whether the set of conditions are sufficient to sterilize the chlorhexidine based antiseptic formulation and the inner surfaces of the sample container.

In some implementations, there is provided a method for determining sterilization conditions for sterilizing a chlorhexidine based antiseptic formulation and a container for medical use, the method comprising: adding the chlorhexidine based antiseptic formulation into a sample container having inner surfaces; applying a detection tab to an inner surface of the container; hermetically sealing the sample container; exposing the sealed sample container to a set of temperature and heating time conditions; removing the detection tab after heat treatment; testing the detection tab for sterility; and determining from results of the testing step whether the set of conditions are sufficient to sterilize the chlorhexidine based antiseptic formulation and the inner surfaces of the sample container.

In some implementations, the sample container has a first region holding the chlorhexidine based antiseptic formulation and a second region comprising air and vapour from the chlorhexidine based antiseptic formulation. In some implementations, the detection tab is applied in the second region.

In some implementations, the process also includes determining from the results of the testing step whether the set of conditions are sufficient to sterilize the chlorhexidine based antiseptic formulation and the second region the container.

In some implementations, there is provided a sterilized chlorhexidine-containing container, comprising a hermetically sealed body having internal heat-sterilized surfaces and holding a heat-sterilized chlorhexidine based antiseptic formulation.

In some implementations, the container comprises: a first region holding a chlorhexidine based antiseptic formulation and having formulation-contacting heat-sterilized inner surfaces; and a second region comprising air and vapour from the chlorhexidine based antiseptic formulation and having vapor-contacting heat-sterilized inner surfaces.

In some implementations, the container is an applicator, a bottle, a swab stick, or a pad-containing pouch.

BRIEF DESCRIPTION OF THE DRAWINGS

FIG. 4 is a process flow diagram for production of sterilized containers.

FIG. 5 is another process flow diagram for determining sterilization conditions.

DETAILED DESCRIPTION

Figure 3:
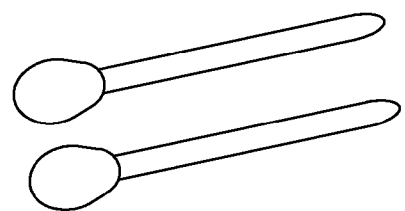
FIG. 3 is a partial transparent view schematic of swabs.

Various techniques are described for sterilizing chlorhexidine based antiseptic formulations and containers used to hold such formulations.

For example, some processes described herein may be used for sterilizing chlorhexidine based antiseptic formulations as well as the containers such as bottles, applicators, swabs, and so on.

Referring to FIG. 4, in some implementations, the process may include adding the chlorhexidine based antiseptic formulation into the container (step 100); sealing the container to form a sealed container, which may have a first region holding the chlorhexidine based antiseptic formulation and a second region comprising air and vapour from the chlorhexidine based antiseptic formulation (step 102); and exposing the sealed container to heat at a temperature and heating time sufficient to sterilize the interior of the container, which may include the chlorhexidine based antiseptic formulation and the second region of the container (step 104). The method may also include shipping the sterilized containers the customers (step 106). It should be noted that the containers may have a second region that does not contain the chlorhexidine based antiseptic formulation, or may be completely filled with the chlorhexidine based antiseptic formulation.

The chlorhexidine based antiseptic formulation may include one or more solvent. Various solvents may be used. Co-solvents may also be used, as well as various additives. The chlorhexidine based antiseptic formulation may include one or more excipients. In some scenarios, the chlorhexidine based antiseptic formulation includes purified water.

The chlorhexidine based antiseptic formulation may include an additional active component. In some scenarios, the additional active component may be an alcohol, which may be a secondary alcohol, such as isopropyl alcohol.

The chlorhexidine based antiseptic formulation may also include chlorhexidine gluconate and may be referred to as "CHG".

The formulation may include the chlorhexidine and other components in various proportions. For example, the chlorhexidine may be present in about 0.5% w/v to about 5 t % w/v, optionally about 1% w/v to about 3.5% w/v, or about 1.5 t % w/v to about 2.5% w/v. The additional active component, such as isopropyl alcohol, may be present in about 55% v/v to about 80% v/v, or about 65% v/v to about 75% v/v, for example. Water may be present as the remainder, and/or in about 15% v/v to about 45% v/v or 20% v/v to about 30 t % v/v. The formulation may contain other additives in various concentrations, for example a dye for tinting the formulation and present in an amount sufficient to provide the desired color.

In some implementations, the temperature and heating time may be determined by a method that will be described with reference to FIG. 5. The method for determining sterilization conditions may include adding the chlorhexidine based antiseptic formulation into a sample container (step 200); applying a detection tab to an inner surface of the head space (corresponding for example to the second region of the sample container) (step 202); sealing the sample container (step 204); exposing the sealed sample container to set(s) of temperature and heating time conditions (step 206); removing the detection tab after the heat treatment (step 208); testing the detection tab for sterility (step 210); and determining from the results of such tests whether the set of conditions were sufficient to sterilize the chlorhexidine based antiseptic formulation and the head space of the container (step 212). It should be noted that various combinations of time and temperature may be used in order to identify various efficient heat sterilization conditions. If the conditions are insufficient for providing sterility, another sample container may be used under different conditions (raising the temperature and/or the heating time, for example). It should also be noted that different types of sample containers may be tested to determine efficient heating times and temperatures for manufacturing each type of sterilized container.

By testing the sterility of the head space, the method of determining the heat treatment conditions may be facilitated since the head space may be more susceptible that the formulation itself or the surfaces of the container that are in contact with the formulation. The head space may be seen as representing the worst case scenario in the container and thus testing the head space provides better assurance of sterility of the entire internal volume of the container. Efficient testing can thus be carried out for various formulations and/or containers, and can determine conditions that are both economic and effective for sterilization.

In some implementations, the process for preparing and sterilizing the formulation-containing container includes providing time and temperature conditions that are predetermined by the above method.

In some implementations, the temperature may be between about 55° C. and about 70° C. and the heating time period may be at least 12 hours, although various other time and temperature conditions may be employed. The heating time and temperature may depend on the type of container, the upstream manufacturing steps, the composition of the chlorhexidine based antiseptic formulation including the content of CHG and the type of solvent.

Figure 2:
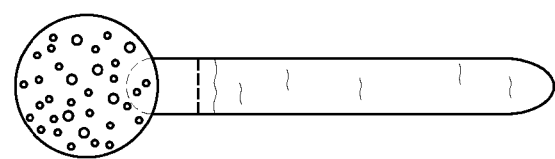
FIG. 2 is a partial transparent side view schematic of another applicator.
Figure 1:
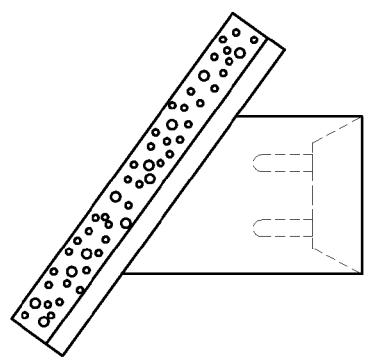
FIG. 1 is a partial transparent side view schematic of an applicator having a head component and a container body component.
Figure 1:
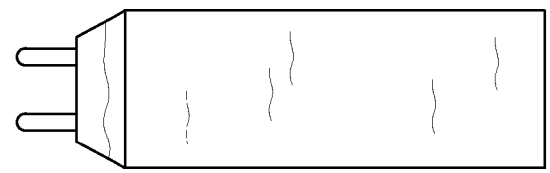

Referring to FIGS. 1 to 3, various different kinds of containers may be used in connection with the process and methods described herein. The containers may include applicators, bottles, pouches and swabs, for example, or any other container that can be hermetically sealed. FIG. 1 illustrates a liquid applicator with a twist function for releasing the liquid from the container body portion into the head component that has the sponge for application. The applicator may be similar to the ones described in U.S. patent application Ser. No. 13/219,054 which is incorporated herein by reference. FIG. 2 illustrates a liquid applicator with an inner barrier that can be broken using various means in order to allow the fluid to flow into the sponge at the far end of the applicator. FIG. 3 illustrates swabs that may be provided within foil packaging, the swabs being squeezable in order to push the liquid into the absorbent end pieces. Other types of containers may also be used.

In terms of sealing the containers, various methods may be possible. For example, the containers may be filled and then a separate end piece may be glued or melt-bonded to form the sealed container. A lock-and-key hermetic sealing assembly or a screw cap arrangement with hermetic sealing capabilities may also be used depending on the type of container.

The container may be completely filled with the liquid formulation or may be partially filled so as to have a vapor region. In the case of applicators and bottles, the vapor region may be referred to as "head space". The vapor region in the container may have various different relative volumes compared to the filled region, depending on the nature of the container. For example, for bottles and applicators, the head space may have a relatively small volume compared to the rest of the container volume, and may be 1% to 5% of the volume for example, although other proportions are also possible. For other types of containers, such as pouches for swab sticks, the vapor region may have larger volume compared to the rest of the container volume, and may be 40% to 95% of the volume for example.

In some scenarios, the container may be a packaging, such as a pouch, that has pads soaked with a CHG formulation for medical use. The entire package, once sealed, may be heat treated in order to sterilize the inner surfaces of the packaging as well as the soaked pads. It should thus be understood that the container may contain items other than the formulation, such as solid material like pads.

The temperature may be selected based on additional criteria, such as to be below the degradation temperature of the CHG and other active components, below any boiling temperatures of the solvent or other components or azeotropes of the formulation, and below the melting, softening or deformation temperature of the container material(s). In some implementations, about 70° C. may be selected as an upper threshold.

The heat treatment may be carried out in a heating chamber with air convection in between a plurality of the containers to ensure uniform heating. Various other heating apparatuses may also be used and may involve conveyors, different heating zones with different or same temperatures, and so on.

EXAMPLES

Experiments were conducted to determine whether heat treatment was able to sterilize containers containing a chlorhexidine based antiseptic formulation.

A formulation was prepared containing CHG, isopropyl alcohol and purified water. The formulation was put into a hermetically sealed container. Exposure to a temperature between 62° C. and 67° C., and the heating time of at least 12 hours, resulted in sterilization of the interior of the container, including surfaces not in direct contact with the formulation.

The invention claimed is:

1. A process for preparing and sterilizing a chlorhexidine based antiseptic formulation and a container for medical use, the process comprising:
    adding the chlorhexidine based antiseptic formulation into the container;
    hermetically sealing the container to form a sealed container having a hermetically sealed interior; and
    exposing the sealed container to heat at a temperature and heating time sufficient to effect heat sterilization of the chlorhexidine based antiseptic formulation and the hermetically sealed interior of the sealed container, wherein sterilization of the chlorhexidine based antiseptic formulation and the hermetically sealed interior of the sealed container consists of the heat sterilization.

2. The process of claim 1, wherein the sealed container comprises a first region holding the chlorhexidine based antiseptic formulation and a second region comprising air and vapour from the chlorhexidine based antiseptic formulation.

3. The process of claim 1, wherein the chlorhexidine based antiseptic formulation comprises a solvent.

4. The process of claim 1, wherein the chlorhexidine based antiseptic formulation comprises purified water.

5. The process of claim 1, wherein the chlorhexidine based antiseptic formulation comprises an additional active component.

6. The process of claim 5, wherein the additional active component is miscible in water.

7. The process of claim 5, wherein the additional active component comprises an alcohol.

8. The process of claim 7, wherein the alcohol is a secondary alcohol having a single hydroxyl group.

9. The process of claim 5, wherein the additional active component is isopropyl alcohol.

10. The process of claim 9, wherein the isopropyl alcohol is present in a concentration between about 55% v/v and about 80% v/v of the chlorhexidine based antiseptic formulation.

11. The process of claim 10, wherein the chlorhexidine is chlorhexidine gluconate.

12. The process of claim 11, wherein the chlorhexidine based antiseptic formulation comprises about 0.5% w/v to about 5% w/v of the chlorhexidine gluconate.

13. The process of claim 11, wherein the chlorhexidine based antiseptic formulation comprises about 1.5% w/v to about 2.5% w/v of the chlorhexidine gluconate.

14. The process of claim 13, wherein the temperature is at least about 62° C. and the heating time is at least about 12 hours.

15. The process of claim 13, wherein the temperature is between about 55° C. and about 70° C. and the heating time is between 9 hours and 36 hours.

16. The process of claim 1, wherein the container is a liquid applicator.

17. The process of claim 16, wherein the liquid applicator comprises:
    a container body component as the sealed container; and
    a head component comprising an absorbent material, the head component being cooperable with the container body component in order to break a portion of the container body component and allow the chlorhexidine based antiseptic formulation to flow from the container body component through the head component and into the absorbent material for application.

18. The process of claim 1, wherein the temperature is at least about 62° C. and the heating time is at least about 12 hours.

19. The process of claim 1, wherein the temperature is between about 55° C. and about 70° C. and the heating time is at least 9 hours.

20. The process of claim 1, wherein the temperature is between about 55° C. and about 70° C. and the heating time is at least 16 hours.

21. The process of claim 1, wherein the temperature is between about 55° C. and about 70° C. and the heating time is at least 24 hours.

22. The process of claim 1, wherein the temperature is between about 55° C. and about 70° C. and the heating time is between 9 hours and 36 hours.

23. The process of claim 1, wherein the temperature is between about 60° C. and about 67° C. and the heating time is at least 12 hours.

24. The process of claim 1, further comprising determining sterilization conditions for the heat sterilization comprising:
- adding the chlorhexidine based antiseptic formulation into a sample container having inner surfaces;
- applying a detection tab to an inner surface of the sample container;
- hermetically sealing the sample container;
- exposing the sealed sample container to a set of temperature and heating time conditions;
- removing the detection tab after heat treatment;
- testing the detection tab for sterility; and
- determining from results of the testing step whether the set of temperature and heating time conditions are sufficient to sterilize the chlorhexidine based antiseptic formulation and the inner surfaces of the sample container.

25. The process of claim 1, wherein:
the chlorhexidine based antiseptic formulation comprises:
1% w/v to 3.5% w/v of chlorhexidine gluconate;
55% v/v to 80% v/v of a secondary alcohol having a single hydroxyl group; and
20% v/v to 30% v/v of purified water;
the temperature is below about 70° C. and the heating time is between 9 hours and 36 hours; and
the hermetically sealed interior of the container comprises:
a filled region containing the chlorhexidine based antiseptic formulation; and
a head space.

26. The process of claim 25, wherein:
the chlorhexidine based antiseptic formulation comprises:
1.5% w/v to about 2.5% w/v of the chlorhexidine gluconate; and
55% v/v to 80% v/v of isopropyl alcohol; and
the head space comprises 1% to 5% volume of the hermetically sealed interior.

27. The process of claim 26, wherein the temperature is between about 55° C. and about 70° C.

* * * * *